United States Patent [19]

Ristaino

[11] Patent Number: 5,780,271

[45] Date of Patent: Jul. 14, 1998

[54] PCR ASSAYS FOR PHYTOPHTHORA SPECIES

[75] Inventor: Jean B. Ristaino, Cary, N.C.

[73] Assignee: North Carolina State University, Raleigh, N.C.

[21] Appl. No.: 748,860

[22] Filed: Nov. 13, 1996

[51] Int. Cl.$^6$ .......................... A61K 38/43; C12P 19/34; C07H 21/04; C07H 21/00

[52] U.S. Cl. ...................... 435/91.2; 424/94.1; 536/22.1; 536/24.3; 536/25.3

[58] Field of Search ................................. 536/22.1, 25.3, 536/24.3; 435/91.2; 424/94.1

[56] References Cited

PUBLICATIONS

O'Donell Ribosomal DNA internal transcribed spacers are highly divergent in the phytopathogenic ascomycete Fusarium sambucinum (Gibberella pulicaris), vol. 22, pp. 213–220, 1992.

T. Érsek et al., "PCR Amplification of Species–Specific DNA Sequences Can Distinguish among Phytophthora Species", Applied and Environemntal Microbiology, Jul. 1994, pp. 2616–2621.

H. Forster et al., "Mitochondrial and Nuclear DNA Diversity within Six Species of Phytophthora", Experimental Mycology, 14, 1990, pp. 18–31.

P.W. Tooley et al; Application of PCR–Based Test for Detection of Potato Late Blight in Tubers Abstract, Potato Association of America meeting held Aug., 1996 P12.

P.W. Tooley and M.M. Carras; Development of PCR primers for the detection of Phytophthora infestans species infection potatoes Phytophthora Infestans 150 European Association for Potato Research, Pathology Section Conference pp. 375 (1995).

J.B. Ristaino et al; PCR Amplification of Ribosomal DNA for Species Identification of Phytophthora Phytopathology 85 1176 (492).

J.B. Ristaino et al; Tracking ancient epidemics: survey of plant pathogens of Preceramic Peru; Phytophthora Infestans 150 European Assoc. for Pto. Research Pathology Section Conference pp. 226–231.

D.E. Fraser et al; Characterisation of Phytophthora infestans isolates from tomato and potato in North Carolina, U.S.A., 1993–1995 Phytophthora Infestans 150 European Assoc. for Pto. Research Pathology Section Conference pp. 102–106 Sep. 1995.

K.F. Falkenstein et al; Differentiation of Group IV Phytophthora Species by PCR Amplification of Nuclear Ribosomal DNA Internal Transcribed Spacer Region 2 Phytopathology 81 No. 10: 1157 (Abstract) (1991).

H. Wang et al; A Simple Method of Preparing plant samples for PCR Nucleic Acids Research 21 No. 17, pp. 4153–4154 (1993).

T.J. White et al; Amplification and Direct Sequencing of Fungal Ribosomal RNA Genes for Phylogenetics PCR Protocols: A Guide to Methods and Application pp. 315–322 (1990).

C.L. Trout et al; Specific Amplification of Phytophtora Infestans with an Oligonucleotide Primer Presented at American Phytopathological Meetings Summer 1996.

J.B. Ristaino et al; PCR Amplification of Ribosomal DNA for Species Identification of Phytophthora; Poster Presentation American Phytopathological Society Meeting Aug. 1995.

E.M. Moller et al; Mitochondrial and Nuclear DNA Restriction Enzyme Analysis of the Closely Related Phytophthora Species P. infestans, P. mirabilis, and P. phaseoli; J. Phytopathology 139, pp. 309–321 (1993).

(List continued on next page.)

Primary Examiner—Kenneth R. Horlick
Assistant Examiner—Joyce Tung
Attorney, Agent, or Firm—Myers Bigel Sibley & Sajovec, L.L.P.

[57] ABSTRACT

Methods of screening for the presence of specific Phytophthora species using oligonucleotide primers are discussed. Specific methods are presented to determine the presence of P. infestans in potato and tomato, and P. cactorum in tomato and other plant species.

21 Claims, 2 Drawing Sheets

OTHER PUBLICATIONS

S.B. Lee et al; *Detection of Phytophthora Species by Oligonucleotide Hybridization to Amplified Ribosomal DNA Spacers; The American Phytopathological Society* 83 No. 2, pp. 177–181 (1993).

P.H. Goodwin et al; *Cloned DNA Probes for Identification of Phytophthora parasitica; Phytopathology* pp. 716–721 (1989).

F. Panabieres et al; *Repetitive DNA Polymorphism Analysis as a Tool for Identifying Phytophthora Species; Molecular Plant Pathology* 79 No. 10, pp. 1105–1109 (1989).

PCR ASSAYS FOR PHYTOPHTHORA SPECIES

This invention was made with Government support under the United States Department of Agriculture's National Research Initiatives Competitive Grant Program, Grant No. 95-37313-1941 and National Science Foundation Grant No. DEB 9417791-01. The Government has certain rights to this invention.

FIELD OF THE INVENTION

The present invention relates to rapid diagnostic or screening assays for species of the fungal pathogen Phytophthora, using oligonucleotide primers.

BACKGROUND OF THE INVENTION

Species of the fungus Phytophthora cause disease worldwide in economically important plants, including potato, pepper, tomato, tobacco, safflower, cucumber, squash, pumpkin, avocado, citrus, strawberry, walnut, apricot, cherry, azalea, rhododendron, camellia, shore juniper and fraser fir. Late blight, a fungal disease caused by the heterothallic, oomycete Phytophthora infestans is an important disease of potatoes and tomatoes worldwide. Prior to 1992 late blight epidemics were infrequent in most parts of the United States and Canada (Fry et al., Plant Dis. 77:653 (1993)). However, in 1992 and 1993 severe late blight epidemics were reported on both tomato and potato throughout the US and Canada; late blight has been reported annually since 1992. Late blight is responsible for large amounts of chemical fungicides applied annually, and the development of fungicide resistance in the late blight pathogen has occurred (Deahl et al., Am. Potato J. 70:779 (1993); Fry et al., Plant Dis. 77:653 (1993); Niederhauser, Ann. Rev. Phytopathol. 31:1 (1993)).

Plant parts infected with the late blight pathogen include potato tubers and tomato fruits, and infected plant parts are likely sources of primary inoculum in fields. (Fry et al., Annu. Rev. Phytopathol. 30:107 (1992); Goodwin et al., Phytopathology 84:533 (1994); Stevenson, Management of early blight and late blight, In: Potato Health Management, RC Rowe (Ed.), American Phytopathology Society, St. Paul, Minn. (pp. 141–147)). Detection of the pathogen inoculum sources prior to planting would prevent introduction of infected material into fields. Multiple species of Phytophthora infect both potato and tomato, making species-specific diagnosis complex. Traditional methods of isolating and identifying Phytophthora species are time-consuming, limiting effectiveness in the field.

SUMMARY OF THE INVENTION

A first object of the present invention is an isolated DNA molecule having SEQ ID NO:1.

A further object of the present invention is a method of screening a sample for the presence of at least one of Phytophthora infestans, Phytophthora cactorum, or Phytophthora mirabilis. The test sample is subjected to a lysing procedure to lyse any fungal cells present and release fungal DNA. The fungal DNA is amplified by PCR using an oligonucleotide primer of SEQ ID NO:1 and an oligonucleotide primer of SEQ ID NO:3. The presence of an approximately 600 base pair amplification product indicates that the test sample contained at least one of P. infestans, P. cactorum or P. mirabilis.

A further object of the present invention is a method of screening potato for Phytophthora infestans, in which a sample of potato is treated as described immediately above. The presence of an approximately 600 base pair amplification product is indicative of P. infestans.

A further aspect of the present invention is a method of screening tomato for the presence of Phytophthora infestans and/or Phytophthora cactorum, in which a sample of tomato is treated as described immediately above. The presence of an approximately 600 base pair amplification product is indicative of either (or both) P. infestans and P. cactorum.

A further aspect of the present invention is a method of screening tomato for the presence of either Phytophthora infestans or Phytophthora cactorum, in which a sample of tomato is treated as described above. If amplification results in an approximately 600 base pair amplification product that can be digested with HaeIII endonuclease, the presence of P. cactorum is indicated. The presence of undigested approximately 600 base pair amplification product indicates the presence of P. infestans.

A further object of the present invention is a method of screening plants, particularly fruit crops and strawberrys, for the presence of Phytophthora cactorum, in which a plant sample is treated as described above. The presence of an approximately 600 base pair amplification product that can be digested with HaeIII endonuclease indicates the presence of P. cactorum.

A further aspect of the present invention is a kit for screening samples for the presence of at least one of Phytophthora infestans, Phytophthora cactorum, and Phytophthora mirabilis, the kit containing an oligonucleotide of SEQ ID NO:1.

The foregoing and other objects and aspects of the present invention are explained in detail in the specification set forth below.

3

Figure 1:
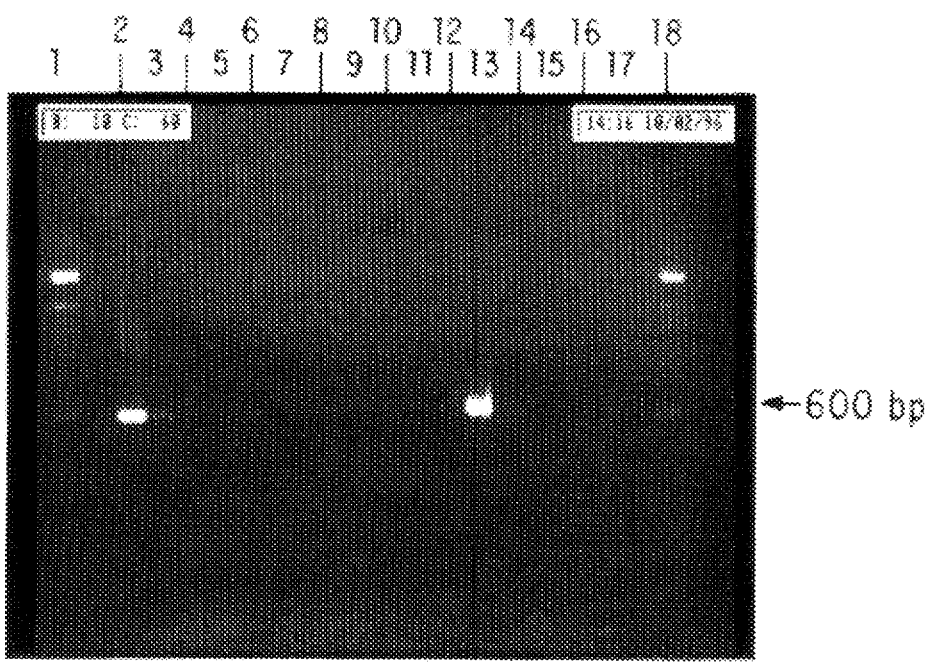
FIG. 1 shows an agarose gel containing PCR amplification products (primers PINF (SEQ ID NO:1) and ITS5 (SEQ ID NO:3)) from representative isolates of fourteen species of Phytophthora and two species of Pythium: P. infestans 94-52 (lane 2); P. cactorum 1298 (lane 3); P. capsici SC1A (lane 4); P. cinnamomi 2301 (lane 5); P. citricola M213 (lane 6); P. citrophthora M-86 (lane 7) P. cryptogea PCR-1 (lane 8); P. drechsleri 34-3-2 (lane 9); P. erythroseptica 10 (lane 10); P. fragariae R-4 (lane 11); P. megasperma NY321 (lane 12); P. mirabilis OS0016 (lane 13); P. nicotianae 332 (lane 14); P. sojae R1 (lane 15); Pythium aphanidermatum L22-3 (lane 16); Pythium irregulare L74-2 (lane 17). Lanes 1 and 18 contained a 100 bp DNA ladder.

(lane 10), tomato fruit lesion from Waynesville N.C. (lane 11), healthy tomato leaf (lane 12). Lanes 1 and 13 contained a 100 bp DNA ladder.

DETAILED DESCRIPTION OF THE INVENTION

The present inventor has developed a rapid and accurate method for specific detection of Phytophthora species.

Molecular tools including isozyme analysis, restriction fragment length polymorphisms in nuclear and mitochondrial DNA, RAPD PCR, serological assays, DNA probes, and PCR of internal transcribed spacer regions (ITS) and nuclear small and large subunit rRNA have been developed to evaluate intraspecific and interspecific variation in Phytophthora species. Ersek et al., *Appl. Environ. Microbiol.* 60:2616 (1994); Forster et al., *Exp. Mycol.* 14:18 (1990); Goodwin et al., *Phytopathology* 79:716 (1989); Lee et al., *Phytopathology* 83:177 (1993); Lee and Taylor, *Mol. Biol. Evol.* 94:636 (1992); Oudemans and Coffey, *Mycol. Res.* 95:1025 (1991); Panabieres et al., *Phytopathology* 79:1105 (1989). Most of these techniques involve isolating the pathogen into pure culture followed by complex extraction procedures to isolate DNA or to examine proteins. Recently, Tooley and Carras reported the development of three sets of PCR primers based on the internal transcribed spacer region (ITS2) of *Phytophthora infestans, Phytophthora erythroseptica* and *Phytophthora nicotianae* (Tooley and Carras, p. 375 In: *Phytophthora infestans* 150—*European Association for Potato Research, Pathology Section Conference*, Dowley et al. (eds.), Boole Press Ltd., Dublin, Ireland (1995)) The work of Tooley and Carras has focused only on isolates infecting potato and it is unclear how specific their primers are within the genus Phytophthora as a whole, or on other plant species Late blight of tomato and potato, caused by *Phytophthora infestans* infection, is a serious agricultural problem. *Phytophthora infestans* is difficult to identify when sporangia or other characteristic morphological structures are absent and may be easily confused with other Phytophthora species. *P. infestans* is also difficult to isolate into pure culture. The present methods: use a quick lysis procedure and subsequent DNA amplification with sample material known to contain, or suspected of containing, a Phytophthora pathogen; are particularly applicable to screening tomato or potato for late blight; are rapid and eliminate the need to isolate the pathogen into pure culture and extract DNA prior to DNA amplification. The present methods, optionally coupled with known or traditional diagnostic methods, provide rapid, accurate diagnosis of late blight infected plant material.

The present inventor amplified ribosomal DNA (rDNA) from four isolates of *P. infestans* representing the four genotypes US1, US6, US7, US8 (based on allozyme analysis; see, e.g., Fraser et al., *Phytopathology* (in press, 1996); Shattock et al., *Phytopathology* 76:410 (1986)) using polymerase chain reaction (PCR) and the universal primers ITS4 (TCCTCCGCTT ATTGATATGC; SEQ ID NO:2) and ITS5 (GGAAGTAAAA GTCGTAACAA GG; SEQ ID NO:3). PCR products were then sequenced using an automated sequencer. Sequences were aligned with published sequences from five other Phytophthora species and a region specific to *P. infestans* was identified by the present inventor and used to construct a PCR primer, termed PINF for *P. infestans*, of SEQ ID NO:1. The inventor screened 101 isolates representing fourteen species of Phytophthora and two species of Pythium with the PINF primer. PCR amplification with primers PINF and ITS5 resulted in amplification of an approximately 600 base pair product only in isolates of *P. infestans, P. mirabilis* and *P. cactorum*. As neither *P. mirabilis* or *P. cactorum* are pathogens of potato, amplification using the PINF primer and a sample of potato are indicative of *P. infestans*. In tomato, both *P. infestans* and *P. cactorum* are known pathogens; *P. mirabilis* is not known as a pathogen of tomato. Thus amplification using the PINF primer and a sample of tomato are indicative of *P. infestans* and/or *P. cactorum*. Restriction digests of the PINF-amplified product allow differentiation between *P. infestans* and *P. cactorum*.

The present methods are carried out by collecting a sample suspected of containing Phytophthora cells, treating the sample to a lysis procedure to release fungal DNA from any cells present in the sample, and then determining the presence or absence of fungal DNA in the sample. Any sample which is suspected of containing the pathogen of interest may be employed, including but not limited to soil, fresh plant parts (such as tomato fruit, tomato plant roots or leaves, potato tubers, potato plant roots or leaves strawberries, or strawberry plant roots or leaves), stored plant parts (such as herbarium samples or stored seed), and residue in shipping or holding containers.

Determining the presence or absence of species specific fungal DNA is carried out using the oligonucleotide primer PINF (SEQ ID NO:1) by means of an amplification reaction such as a polymerase chain reaction. The PINF primer is used in combination with one of the universal internal transcribed spacer (ITS) region primers. The PINF primer may be used with any one of ITS1, ITS3, or ITS5; use of the combination of ITS5 and PINF is presently preferred as this provides a larger amplification product than use of PINF with either of the other two ITS primers.

The product of the amplification reaction may then be detected by running an electrophoretic gel or detection with a fluorescent label, or a number of other techniques, as are known in the art.

The amplification of the target nucleic acid sequence may be carried out by any suitable means, as are known in the art. See generally D. Kwoh and T. Kwoh, *Am. Biotechnol. Lab.* 8, 14–25 (1990). An example of a suitable amplification technique is polymerase chain reaction (PCR). Polymerase chain reaction is currently preferred. Advantages of PCR include that the fungal organisms need not be cultured prior to detection by PCR, and the sensitivity and rapidity of the technology.

DNA amplification techniques used in the methods of the present invention involve the use of the PINF oligonucleotide (SEQ ID NO:1) which specifically binds to the DNA of a limited, known number of Phytophthora species under the same hybridization conditions. DNA amplification products obtained using the PINF oligonucleotide in the amplification process can be digested with restriction enzymes; the resulting restriction digests further distinguish among Phytophthora species, as discussed below.

Polymerase chain reaction (PCR) may be carried out in accordance with known techniques. See, e.g., U.S. Pat. Nos. 4,683,195; 4,683,202; 4,800,159; and 4,965,188. (US Patents cited herein are incorporated by reference herein in their entirety.) In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product, the probe carrying a detectable label, and then detecting the label in accordance with known techniques, or by direct visualization on a gel. When PCR conditions allow for amplification of DNA from more than one Phytophthora species, the species can be distinguished by restriction endonuclease digestion and gel electrophoresis. The source of the sample being tested will also contribute to the identification of Phytophthora species, as it is known that certain species of Phytophthora do not infect certain plants.

Isolated nucleotide molecules having or comprising the sequence provided herein as SEQ ID NO:1 are useful in diagnosis of or screening for the presence of the Phytophthora species *P. infestans*, *P. mirabilis* and/or *P. cactorum*. Such nucleotide molecules are referred to herein as "PINF primers".

As used herein, "samples" suitable for use in the methods of the present invention include any sample suspected of containing Phytophthora, including but not limited to plant tissues known or suspected of containing Phytophthora species, soil or potting materials, packing materials, and residues from packing crates or other containers. Plant tissue samples are preferred. Plant tissue samples may be taken from fruit, shoot, root, leaf or other anatomic sites, as would be apparent to one skilled in the art. Selection of the appropriate sample will be guided in part by the particular Phytophthora species being sought; for example, *P. infestans* is tuber-borne and may not be present in soil.

As used herein, "potato" refers to *Solanum tuberosum*, both complete plants and the edible tuber therefrom. As used herein, "tomato" refers to *Lycopersicon esculentum*, both complete plants and the edible fruit therefrom. As used herein, "strawberry" refers to plants of the genus Fragaria, both complete plants and the edible fruit (berry) therefrom.

As used herein, screening means testing samples for the presence of the specific Phytophthora species (*P. infestans*, *P. mirabilis* and *P. cactorum*) whose DNA binds to the PINF primer, or is capable of amplification by the PINF primer. A negative result (no binding or amplification) indicates the absence of these pathogens; a positive result indicates the presence of at least one of the three pathogens. Screening for the presence of a specific species of Phytophthora (in samples which may have more than one of the above three species present) involves further steps, such as restriction digestion of a PCR amplification product.

As used herein, the "presence" of Phytophthora refers to both the active infection of plant material by this fungal pathogen, as well as the contamination of non-plant materials by Phytophthora. Thus both plant material samples, as well as non-plant samples such as soil or packing material, may be screened for the presence of Phytophthora using the methods of the present invention.

Traditional diagnostic methods for Phytophthora may optionally be combined with the methods of the present invention in a screening program, including but not limited to visual examination of affected plants or microscopic examination of affected plant parts to determine pathogen morphology, and assessment of growth characteristics of fungal samples, pathogenicity assays, physiological tests, and isolation and culture of fungus. However, the present methods are particularly useful in testing materials which do not show visible morphological signs of infection.

The present methods are particularly useful in screening plant species which are known to be susceptible to only one of the following three species of Phytophthora: *P. infestans*, *P. mirabilis* and *P. cactorum* (but may be susceptible to other species of Phytophthora, for example as indicated on Table 1). For example, of these three species only *P. infestans* is known to infect potato, although potato may also be infected by *P. erythroseptica* or *P. nicotianae* as shown on Table 1. Of these three species, only *P. cactorum* is known to infect strawberries, although strawberries are also susceptible to *P. citricola*. In screening such plants using amplification by the PINF and ITS5 primers, the production of an approximately 600 base pair product indicates the presence of at least one of *P. infestans*, *P. mirabilis* and *P. cactorum*. Thus, screening potato plant samples with the PINF oligonucleotide of the present invention is specific for the presence of *P. infestans*, whereas screening strawberries is specific for the presence of *P. cactorum*.

The present methods are also useful in screening plant species (such as tomato) which are known to be susceptible to infection by *P. infestans* and *P. cactorum*, but not *P. mirabilis* (but which may be susceptible to other species of Phytophthora, for example as indicated on Table 1). In screening such plants using amplification by the PINF and ITS5 primers, the production of an approximately 600 base pair product indicates the presence of either (or both) *P. infestans* or/and *P. cactorum*; restriction digests of the DNA amplification products may then be used to differentiate *P. infestans* from *P. cactorum* (HaeIII digests *P. cactorum* but not *P. infestans*).

In screening plant species which are susceptible to infection by each of *P. infestans*, *P. mirabilis* and *P. cactorum* (and which may be susceptible to other species of Phytophthora as well), restriction digests of the approximately 600 base pair PINF/ITS5 amplification product may be used to distinguish between *P. cactorum* and the other two species, but is not useful in distinguishing between *P. infestans* and *P. mirabilis*.

Plants known to be susceptible to *P. cactorum* infection include those in 154 genera and 54 families of vascular plants. See, e.g., Farr et al., *Fungi on plants and plant products in the United States*, the American Phytopathological Society, St. Paul, Minn. (1989). Strawberry and apple are each susceptible to *P. cactorum* infection, and are suitable for screening by the methods of the present invention.

The present methods are of particular use in diagnosing fungal infections in tomato, strawberry and potato plant tissues. Using the PINF primer of the present invention (SEQ ID NO:1) with the ITS5 primer (SEQ ID NO:3) for amplification results in an approximately 600 base pair amplification product when DNA from *P. infestans*, *P. mirabilis* or *P. cactorum* is present in a sample. Of these three species, only *P. infestans* has been reported to infect potato and only *P. cactorum* has been reported to infect strawberries, while only *P. infestans* and *P. cactorum* have been reported to infect tomato (see, e.g., Farr D. F., Bills G. F., Chamuris G. P. and Rossman A. Y.: *Fungi on Plants and Plant Products in the United States*. American Phytopathological Society, St. Paul). *P. mirabilis* is reported as specific to *Mirabilis jalapa* in Mexico and is not a pathogen of potato (Galindo and Hohl, *Sydowia* 38:87–96 (1985)). Results of molecular studies have indicated that *P. mirabilis* and *P. infestans* are closely related (Falkenstein et al., *Phytopathology* 81:1157 (1991); Moller et al., *J. Phytopathol.* 139:309–321 (1993)). Some researchers suggest that *P. mirabilis* should be considered a forma specialis of *P. infestans*.

Farr et al., in *Fungi on Plants and Plant Products in the United States*, American Phytopathological Society, St. Paul, list five species of Phytophthora that infect potato and eight species that infect tomato. The present inventor studied isolates representing the five species of Phytophthora known to infect potato (*P. infestans, P. cryptogea, P. drechsleri, P. erythroseptica*, and *P. nicotianae* var. *parasitica*); only *P. infestans* isolates yielded amplification products when the present PINF primer was utilized with ITS5 primer. These same five isolates were differentiated to species using restriction digestion of ribosomal DNA amplified with the universal primers ITS4 (SEQ ID NO:2) and ITS5 (SEQ ID NO:3) (Ristaino et al., (Abstract) *Phytopathology* 85:1176 (1995)).

Of the eight species of Phytophthora known to infect tomato, seven species (*P. infestans, P. cactorum, P. capsici, P. cinnamomi, P. cryptogea, P. drechsleri* and *P. nicotianae*) were examined by the present inventor. Only *P. infestans* and *P. cactorum* yielded amplification products with PINF/ITS5 primers, and restriction digests of the amplification product with HaeIII differentiated *P. infestans* and *P. cactorum*. Isolates representing seven of the species known to infect tomato were differentiated to species using restriction digestion of rDNA amplified with the universal primers ITS4 and ITS5 (Ristaino et al., (Abstract) *Phytopathology* 85:1176 (1995)).

Three species of Phytophthora known to infect strawberries were examined by the present inventor (*P. cactorum, P. citricola* and *P. fragariae*); only *P. cactorum* yielded amplification products with PINF/ITSS primers.

The present procedure for detecting *P. infestans* in plant tissue comprises lysing fungal cells present in sample material to release fungal DNA, in preparation for DNA amplification by procedures such as Polymerase Chain Reaction (PCR). A suitable lysis method for plant material samples is the quick sodium hydroxide (NaOH) lysis procedure in which a few milligrams of plant tissue is ground (a Konte pestle attached to a hand drill is suitable for grinding) in 0.5N NaOH (10 µl/mg sample), then immediately transferring a portion of this extract to a sterile tube for an approximately 1:100 dilution with 100 mM Tris Buffer, pH 8.0 (for example, 5 µl of ground extract is transferred to a sterile 1.5 ml tube containing 495 µl 100 mM Tris (i.e., an approximately 1:100 dilution with 100 mM Tris (hydroxymethyl) aminomethane, pH 8.0). See Wang et al., *Nucl. Acids Res.* 21:4153 (1993). For PCR, one microliter of the final lysed extract can be used as the DNA template. Where soil samples are being tested, the soil may be subjected to the same lysis procedure as described above for plant tissue samples. Additional suitable lysing procedures will be readily apparent to those skilled in the art.

Kits for carrying out the methods of the present invention may be produced in a number of ways. In one embodiment, the kit comprises the PINF oligonucleotide primer of SEQ ID NO:1. Such kits may further include any one or any combination of: the ITS5 oligonucleotide primer, HaeIII restriction endonuclease, positive control reagents (such as a DNA molecule with a sequence known to bind to PINF, or known to be amplified with PINF and ITS5) and negative control reagents (lacking DNA which is known to bind to PINF or known to be amplified by PINF/ITS5 primers). Ancillary solutions and reagents may optionally be included. Such screening or diagnostic kits may be packaged in any suitable manner, typically with all elements in a single container along with a sheet of printed instructions for carrying out screening tests.

The following examples are provided to illustrate the present invention, and should not be construed as limiting thereof.

EXAMPLE 1

Materials and Methods

Source of isolates: *P. infestans* isolates were collected from diseased potato and tomato plants in North Carolina, Tennessee and South Carolina. (See Fraser D. E., Phenotypic and genotypic diversity of isolates of *Phytophthora infestans* from North Carolina and evaluation of tomato breeding lines for resistance to late blight; Master's thesis, North Carolina State University, Raleigh, N.C., 94 pp. (1996); Fraser et al., Characterization of *Phytophthora infestans* isolates from tomato and potato in North Carolina, pages 102–106 in *Phytophthora infestans* 150—European Association for Potato Research, Pathology Section Conference, L. J. Dowley, et al. (Eds.), Boole Press, Ltd., Dublin, Ireland (1995); Fraser D. E., Shoemaker P. B. and Ristaino J. B., *Phytopathology* (in press 1996)). These isolates are maintained in a collection at North Carolina State University, Department of Plant Pathology. Additional fungal cultures were donated by various individuals. A list of isolates is provided in Table 1.

DNA extraction: Mycelia of each isolate was obtained by growth in pea broth (120 g frozen peas per liter sterile distilled water) at 18°–25° C. (temperature isolate dependent) for at least one week. Mycelia were harvested by filtration and frozen at −20° C. DNA was extracted from mycelia using a CTAB procedure. Frozen mycelia were placed in sterile 1.5 ml microcentrifuge tubes and 150 µl extraction buffer (0.35M sorbitol, 0.1M Tris, 0.005M EDTA, pH 7.5, 0.02M sodium bisulfite) was added and tubes were vortexed. Nuclei lysis buffer (150 µl) containing 0.2M Tris, 0.05M EDTA, pH 7.5, 2.0M NaCl and 2% CTAB (hexadecyltrimethylammonium bromide) was added followed by 60 µl of 5% sarkosyl (5 g N-lauryl sarcosine per 100 ml water) and tubes were vortexed then incubated at 65° C. for 15 to 30 minutes. Chloroform:isoamyl alcohol (300 µl of 24:1) was added to each tube and centrifuged for 15 minutes (13,000×gravity) at room temperature. The aqueous phase was removed to a new tube and the chloroform extraction was repeated. DNA was precipitated overnight at −20° C. in 0.1 volumes of 3M sodium acetate, pH 8.0 and two volumes of cold 100% ethanol. The supernatant was discarded, the pellets were washed with 70% ethanol and then dried under vacuum centrifugation. DNA was resuspended in Te (10 mM Tris-HCl, 0.1 mM EDTA, pH 8.0). Using the above procedure, genomic DNA was extracted from isolates 95-6, 94-52, 94-53, and 95-7 (representing the genotypes US1, US6, US7 and US8, respectively, of *Phytophthora infestans*).

Polymerase Chain Reaction: PCR was conducted in 50 µl reaction volumes. Each reaction consisted of approximately 1 ng of template DNA, 5 µl 10×PCR buffer (Boehringer Mannheim, Indianapolis, Ind.), 36 µl sterile distilled water, 2 µl 1.25–2.0 mM dNTPs (Pharmacia Biotech, Piscataway, N.J.), 2 µl 10 mM $MgCl_2$ (Sigma, St. Louis, Mo.), 2 µl each of 10 µm ITS4 (SEQ ID NO:2) and ITS5 (SEQ ID NO:3) primers (White et al., pp. 315–322 in: *PCR protocols: A guide to methods and applications*, Innis et al. (eds), Academic Press, San Diego (1990)), and 0.4 µl Taq polymerase (5 U/µl, Boehringer Mannheim). All reactions were overlaid with sterile mineral oil prior to thermal cycling. Thermal cycling parameters were initial denaturation at 96° C. for 2 minutes, followed by 35 cycles consisting of denaturation at 96° C. for 1 minute, annealing at 55° C. for 1 minute and extension at 72° C. for 2 minutes. A final extension at 72° C. for 10 minutes followed. Negative controls (no template DNA) were used in every experiment to test for the presence of contaminants in reagents. DNA from each of the four *P. infestans* isolates recited above was used as template in PCR reactions (primers ITS4 and ITS5) targeting the internal transcribed spacers and 5.8S ribosomal RNA gene of the ribosomal DNA repeat.

Amplified products were purified using GeneClean (Bio 101, Vista, Calif.) according to manufacturer's recommendations. PCR products were sent to Iowa State University (Ames, Iowa) for automated DNA sequencing on an ABI Prism System automated sequencer (Model 377, version 2.1.1; Perkin Elmer, Norwalk, Conn.). Sequences were aligned with published sequences from five other Phytophthora species (*P. capsici, P. cinnamomi, P. citrophthora, P. megakarya* and *P. palmivora*; Lee and Taylor, *Mol. Biol. Evol.* 94:636 (1992)) using CLUSTAL V (Higgins and Sharp, *CABIOS* 5:151 (1989)). A region within the internal transcribed spacer region 2 was identified as specific to *P. infestans* (sequence CTCGCTACAA TAGGAGGGTC (5' to 3', Tm=66), SEQ ID NO:1) and used to design and construct a PCR primer (CTCGCTACAA TAGGAGGGTC)(SEQ ID NO:1). The PINF primer was synthesized by Gibco BRL (Gaithersburg, Md.). PCR conditions used with the PINF primer were identical to those described above except that primers PINF and ITS5 (SEQ ID NO:3) were used.

Restriction digestion: Where amplified fragments were digested with restriction enzymes, restriction digests consisted of 3 µl of enzyme mixture (1 µl of REact buffer (Gibco BRL, Gaitherburg, Md.), 1 µl of restriction enzyme, and 8 µl of sterile distilled water) to 30 µl of amplified PCR product. DNA was digested at 37° C. for 1.5 hours followed by 65° C. for 10 minutes. Digested DNA was electrophoresed on agarose gels at 25 milliamps for 3 hours. Gels were stained in ethidium bromide (0.5 µg/ml) to visualize polymorphisms in amplified DNA fragments.

TABLE 1

| ISOLATE | SPECIES | HOST | PRODUCT WITH PINF |
|---|---|---|---|
| 94-52 | P. infestans | Potato | + |
| 94-53 | P. infestans | Potato | + |
| 93-2 | P. infestans | Tomato | + |
| 93-1 | P. infestans | Tomato | + |
| 93-4 | P. infestans | Tomato | + |
| 93-5 | P. infestans | Tomato | + |
| 94-8-1 | P. infestans | Potato | + |
| 94-7 | P. infestans | Potato | + |
| 94-19 | P. infestans | Tomato | + |
| 94-37 | P. infestans | Potato | + |
| 95-6 | P. infestans | Potato | + |
| 95-7 | P. infestans | Potato | + |
| 94-1 | P. infestans | Potato | + |
| 188.1.1 | P. infestans | Potato | + |
| 336.1.4 | P. infestans | Potato | + |
| 342.1.1 | P. infestans | Potato | + |
| 268.1.5 | P. infestans | Potato | + |
| 2.1.3 | P. infestans | Potato | + |
| ME920094 | P. infestans | Potato | + |
| ME880153 | P. infestans | Potato | + |
| CA920008 | P. infestans | Potato | + |
| US920141 | P. infestans | Potato | + |
| 96-3-1 | P. infestans | Potato | + |
| 96-3-2 | P. infestans | Potato | + |
| 96-5 | P. infestans | Potato | + |
| 18/94 | P. infestans | Potato | + |
| 32/94 | P. infestans | Potato | + |
| 51/94 | P. infestans | Potato | + |

TABLE 1-continued

| ISOLATE | SPECIES | HOST | PRODUCT WITH PINF |
|---|---|---|---|
| 57/94 | P. infestans | Potato | + |
| 11/95 | P. infestans | Potato | + |
| 24/95 | P. infestans | Potato | + |
| 31/95 | P. infestans | Potato | + |
| 127/77 | P. cactorum | Unknown | + |
| 234/81 | P. cactorum | Unknown | + |
| 1298 | P. cactorum | Unknown | + |
| SC1A | P. capsici | Pepper | − |
| 18 | P. capsici | Pepper | − |
| 28 | P. capsici | Pepper | − |
| B1HB14 | P. capsici | Pepper | − |
| B2HH4 | P. capsici | Pepper | − |
| 2301 | P. cinnamomi | Rhododendron | − |
| 2302 | P. cinnamomi | Fraser Fir | − |
| 2322 | P. cinnamomi | Camellia | − |
| 2325 | P. cinnamomi | Shore Juniper | − |
| 2337 | P. cinnamomi | Azalea | − |
| 2349 | P. cinnamomi | Leucothe | − |
| 34-2-8 | P. cinnamomi | Walnut | − |
| 34-1-1 | P. citricola | Walnut | − |
| M213 | P. citricola | Avocado | − |
| M215 | P. citricola | Avocado | − |
| M220 | P. citricola | Avocado | − |
| M265 | P. citricola | Avocado | − |
| M266 | P. citricola | Avocado | − |
| 34-4-7 | P. citrophthora | Citrus | − |
| M86 | P. citrophthora | Citrus | − |
| M139 | P. citrophthora | Citrus | − |
| M140 | P. citrophthora | Citrus | − |
| M189 | P. citrophthora | Citrus | − |
| M259 | P. citrophthora | Citrus | − |
| 34-1-7 | P. cryptogea | Safflower | − |
| PCR-1 | P. cryptogea | Safflower | − |
| 34-3-2 | P. drechsleri | Unknown | − |
| 4 | P. erythroseptica | Potato | − |
| 10 | P. erythroseptica | Potato | − |
| 11 | P. erythroseptica | Potato | − |
| A-8 | P. fragariae | Strawberry | − |
| R-4 | P. fragariae | Strawberry | − |
| NC-1 | P. fragariae | Strawberry | − |
| R-1 | P. fragariae | Strawberry | − |
| R-6 | P. fragariae | Strawberry | − |
| NY318 | P. megasperma | Raspberry | − |
| NY321 | P. megasperma | Raspberry | − |
| NY222 | P. megasperma | Apricot | − |
| NY344 | P. megasperma | Cherry | − |
| NY346 | P. megasperma | Cherry | − |
| NY412 | P. megasperma | Peach | − |
| 33-2-9 | P. megasperma | Apple | − |
| OS0016 | P. mirabilis | Mirabilis jalapa | + |
| Rmt6 | P. nicotianae | Tobacco | − |
| 332 | P. nicotianae | Tobacco | − |
| 340 | P. nicotianae | Tobacco | − |
| 335 | P. nicotianae | Tobacco | − |
| 435 | P. nicotianae | Tobacco | − |
| 1-3A | P. nicotianae | Tomato | − |
| 6-1A | P. nicotianae | Tomato | − |
| 5-3A | P. nicotianae | Tomato | − |
| 2HB | P. nicotianae | Tomato | − |
| 6-H | P. nicotianae | Tomato | − |
| 2107 | P. nicotianae | Boxwood | − |
| 2127 | P. nicotianae | Vinca | − |
| 2109 | P. nicotianae | Rhododendron | − |
| 2116 | P. nicotianae | Rhododendron | − |
| 2121 | P. nicotianae | Azalea | − |
| R1 | P. sojae | Soybean | − |
| R3 | P. sojae | Soybean | − |
| R4 | P. sojae | Soybean | − |
| R8 | P. sojae | Soybean | − |
| R13 | P. sojae | Soybean | − |
| R25 | P. sojae | Soybean | − |
| L22-3 | Pythium aphanidermatum | Cucumber | − |
| L74-2 | Pythium irregulare | Turf Grass | − |

EXAMPLE 2

Sequence Analysis

Sequences from the internal transcribed spacer region 2 of *P. infestans* isolates 94-52, 94-53, 95-6 and 95-7 were aligned with published sequences of *P. capsici*, *P. cinnamomi*, *P. citrophthora*, *P. megakarya* and *P. palmivora* (Lee and Taylor, *Mol. Biol. Evol.* 94:636 (1992)). A twenty base sequence (SEQ ID NO:1) was identified in *P. infestans* and a potential *P. infestans* specific primer (PINF, SEQ ID NO:1) was synthesized.

EXAMPLE 3

Amplification with PINF

One hundred and one isolates representing fourteen species of Phytophthora and two species of Pythiumn (Table 1) were examined in PCR reactions with primers PINF (SEQ ID NO:1) and ITS5 (SEQ ID NO:3). FIG. 1. PCR conditions were as described in Example 1. Amplification products were electrophoresed on 1.6% agarose gels containing 0.5 μg/ml ethidium bromide with 1×TBE running buffer. An 100 base pair DNA ladder (Gibco BRL) was included on each gel as a molecular size standard.

Amplification of isolates of *P. infestans*, *P. cactorum* and *P. mirabilis* with PINF and ITS5 yielded a product of approximately 600 base pairs (bp). No product was amplified with isolates of any of the other eleven Phytophthora species or the two Pythium species tested. FIG. 1 is an agarose gel containing PCR amplification products (primers PINF and ITS5) from representative isolates of fourteen species of Phytophthora and two species of Pythium: *P. infestans* 94-52 (lane 2); *P. cactorum* 1298 (lane 3); *P. capsici* SC1A (lane 4); *P. cinnamomi* 2301 (lane 5); *P. citricola* M213 (lane 6); *P. citrophthora* M-86 (lane 7) *P. cryptogea* PCR-1 (lane 8); *P. drechsleri* 34-3-2 (lane 9); *P. erythroseptica* 10 (lane 10); *P. fragariae* R-4 (lane 11); *P. megasperma* NY321 (lane 12); *P. mirabilis* OS0016 (lane 13); *P. nicotianae* 332 (lane 14); *P. sojae* R1 (lane 15); *Pythium aphanidermatum* L22-3 (lane 16); *Pythium irregulare* L74-2 (lane 17). Lanes 1 and 18 contained a 100 base pair DNA ladder (Gibco BRL) as a molecular size standard.

Figure 2:
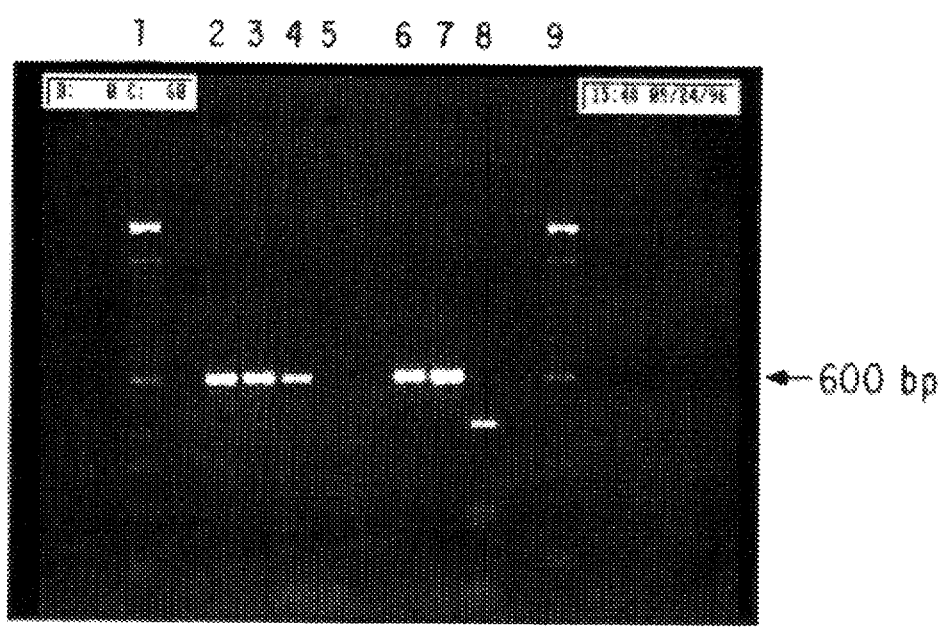
FIG. 2 shows the results of PINF amplification of P. infestans, P. mirabilis, and P. cactorum, and HaeIII restriction digestion of the approximately 600 base pair PCR product. Lanes 2, 3, and 4: PINF amplification products of P. infestans, P. mirabilis, and P. cactorum, respectively. Lane 5: no template DNA control. Lanes 6, 7 and 8: HaeIII digests of PINF amplification products of P. infestans, P. mirabilis, and P. cactorum, respectively. Lanes 1 and 9 contained a 100 bp DNA ladder.

Restriction digests were performed on the approximately 600 bp amplified products from *P. infestans*, *P. mirabilis* and *P. cactorum* to differentiate isolates of these species (FIG. 2). The approximately 600 base pair product amplified from *P. cactorum* using primer PINF was digested with HaeIII, however, the amplification products of *P. infestans* and *P. mirabilis* were not. Restriction digests with additional endonucleases did not differentiate *P. infestans* from *P. mirabilis*.

As shown on FIG. 2, PINF amplification of *P. infestans*, *P. mirabilis*, and *P. cactorum*, with HaeIII restriction digestion of the approximately 600 base pair product, differentiates *P. infestans* from *P. cactorum*. Lanes 2, 3, and 4: PINF amplification products of *P. infestans*, *P. mirabilis*, and *P. cactorum*, respectively. Lane 5: no template DNA control. Lanes 6, 7 and 8: HaeIII digests of PINF amplification products of *P. infestans*, *P. mirabilis*, and *P. cactorum*, respectively. Lanes 1 and 9 contained a 100 base pair DNA ladder (Gibco BRL) as a molecular size standard.

EXAMPLE 4

Amplification from Diseased Tissue

Lesions obtained from late blight diseased potato plants collected in Pasquotank and Yadkin Counties in North Carolina in 1996 and from late blight diseased tomato leaves and fruits collected in Fletcher and Waynesville, North Carolina in 1996 were excised and subjected to a NaOH lysis as preparation for PCR according to the method of Wang et al., *Nucl. Acids Res.* 21:4153 (1993). In addition, potato tuber slices were inoculated with pure culture *P. infestans* in the laboratory and after approximately one week small tuber pieces were lysed with NaOH for subsequent PCR. Healthy leaf pieces from tomato and healthy potato tuber pieces were included in the NaOH extractions and subsequent PCR reactions as controls. The NaOH lysis procedure consisted of grinding a few milligrams of plant tissue in 0.5N NaOH (10 μl/mg) then immediately transferring 5 μl of this extract to a sterile 1.5 ml tube containing 495 μl 100 mM Tris, pH 8.0. One microliter of this extract was used as the DNA template for PCR. The conditions for PCR were identical to those described above for amplification with the PINF primer. PCR reactions were repeated at least two times. *Phytophthora infestans* was isolated into pure culture from the diseased tissue by isolating sporangia and transferring to Rye B agar (extract from 60 grams of rye grains, 20 grams sucrose, 15 grams agar, 0.05 grams β-sitosterol per liter).

Figure 3:
FIG. 3 shows amplification of the approximately 600 base pair product obtained from P. infestans infected potato and tomato using the PINF primer. P. infestans 94-52 pure culture (lane 2), potato leaf lesion from Pasquotank Co. (lanes 3 and 4), potato leaf lesion from Yadkin Co. (lane 5), potato tuber inoculated with P. infestans isolate 94-52 (lane 6), healthy potato tuber (lane 7), tomato leaf lesion from Fletcher, N.C. (lane 8), tomato fruit lesion from Fletcher, N.C. (lane 9), tomato leaf lesion from Waynesville N.C.

FIG. 3 shows the PCR amplification of an approximately 600 base pair product obtained from late blight infected potato and tomato using the PINF primer as described above. *P. infestans* 94-52 pure culture (lane 2), potato leaf lesion from Pasquotank Co. (lanes 3 and 4), potato leaf lesion from Yadkin Co. (lane 5), potato tuber inoculated with isolate 94-52 (lane 6), healthy potato tuber (lane 7), tomato leaf lesion from Fletcher, N.C. (lane 8), tomato fruit lesion from Fletcher, N.C. (lane 9), tomato leaf lesion from Waynesville N.C. (lane 10), tomato fruit lesion from Waynesville N.C. (lane 11), healthy tomato leaf (lane 12). Lanes 1 and 13 contained a 100 base pair DNA ladder (Gibco BRL) as a molecular size standard.

A single PCR product approximately 600 base pairs in size was detected in late blight infected tomato and potato samples (FIG. 3) using the primers PINF and ITS5. The presence of *P. infestans* in the diseased plants was confirmed by isolating the fungus from the tissue into pure culture.

EXAMPLE 5

Amplification from Herbarium Samples

Specimens of potato leaves and tubers collected in the early 1900s were obtained from the herbarium collection of G. P. Clinton of the Connecticut Agricultural Experiment Station. These specimens were labelled as containing oospores of *P. infestans*.

The herbarium specimens were examined under brightfield microscopy and sporangiophores and oospores typical of *P. infestans* were observed. DNA was extracted from a portion of each of the herbarium specimens and was successfully amplified with the PINF primer of SEQ ID NO:1, as described above. These results provide molecular evidence of *P. infestans* in potato leaves and tubers collected in the early 1900s, and demonstrate the use of the PINF primer in non-fresh plant samples.

The foregoing is illustrative of the present invention and is not to be construed as limiting thereof. The invention is defined by the following claims, with equivalents of the claims to be included therein.

---

That which is claimed is:

1. An isolated DNA molecule having SEQ ID NO:1.

2. An isolated DNA molecule of claim 1, wherein said DNA molecule is coupled to a detectable label.

3. A molecule of claim 2 wherein said detectable label is selected from the group consisting of radioisotopes, fluorescent dyes and enzymes.

4. A method of screening a sample for the presence of at least one of the Phytophthora species selected from the group consisting of *Phytophthora infestans, Phytophthora cactorum,* and *Phytophthora mirabilis*, comprising the steps of:

a) obtaining a test sample;

b) lysing any fungal cells present in the test sample to release fungal DNA; and c) amplifying any fungal DNA present by PCR using an oligonucleotide primer of SEQ ID NO:1 and an oligonucleotide primer of SEQ ID NO:3;

wherein an approximately 600 base pair amplification product indicates the presence of at least one of *P. infestans, P. cactorum* or *P. mirabilis* in the test sample.

5. The method of claim 4 wherein said test sample is selected from the group consisting of tomato fruit, tomato plant, potato tuber, potato plant, strawberry fruit, strawberry plant, apple fruit and apple plant.

6. The method of claim 4 wherein said lysing step comprises:

a) grinding said sample in sodium hydroxide; and b) diluting said sample with Tris(hydroxymethyl) aminomethane buffer.

7. The method of claim 4, further comprising restriction endonuclease digestion of said approximately 600 base pair amplification product by HaeIII endonuclease, wherein digestion of said amplification product indicates the presence of *P. cactorum*.

8. A method of screening potato for *Phytophthora infestans*, comprising the steps of:

a) obtaining a potato sample;

b) lysing any fungal cells present in the potato sample to release fungal DNA; and c) amplifying any fungal DNA present by PCR using an oligonucleotide primer of SEQ ID NO:1 and an oligonucleotide primer of SEQ ID NO:3;

wherein an approximately 600 base pair amplification product indicates the presence of *P. infestans* in the sample.

9. The method of claim 8 wherein said potato sample is selected from the group consisting of potato tuber, potato plant leaf, potato plant stem, and potato plant root.

10. A method of screening tomato for the presence of Phytophthora species selected from the group consisting of *Phytophthora infestans* and *Phytophthora cactorum*, comprising the steps of:

a) obtaining a tomato sample;

b) lysing any fungal cells present in the tomato sample to release fungal DNA; and c) amplifying any fungal DNA present by PCR using an oligonucleotide primer of SEQ ID NO:1 and an oligonucleotide primer of SEQ ID NO:3;

wherein an approximately 600 base pair amplification product indicates the presence of at least one of *P. infestans* and *P. cactorum* in the tomato sample.

11. The method of claim 10 wherein said tomato sample is selected from the group consisting of tomato fruit, tomato plant leaf, tomato plant stem, and tomato plant root.

12. The method of claim 10 wherein said lysing step comprises:

a) grinding said sample in sodium hydroxide; and b) diluting said sample with Tris(hydroxymethyl) aminomethane buffer.

13. The method of claim 10, further comprising restriction endonuclease digestion of said approximately 600 base pair amplification product by HaeIII endonuclease, wherein digestion of said amplification product indicates the presence of *P. cactorum*.

14. A method of screening tomato for the presence of Phytophthora species selected from *P. infestans* and *P. cactorum*, comprising the steps of:

a) obtaining a tomato sample;

b) lysing any fungal cells present in the tomato sample to release fungal DNA;

c) amplifying any fungal DNA present by PCR using an oligonucleotide primer of SEQ ID NO:1 and an oligonucleotide primer of SEQ ID NO:3; and d) digesting any approximately 600 base pair amplification product from step (c) with HaeIII endonuclease;

wherein digestion of the approximately 600 base pair amplification product by HaeIII endonuclease indicates the presence of *P. cactorum* in the tomato sample, and undigested approximately 600 base pair amplification product indicates the presence of *P. infestans*.

15. The method of claim 14 wherein said test sample is selected from the group consisting of tomato fruit, tomato plant leaf, tomato plant stem, and tomato plant root.

16. The method of claim 14 wherein said lysing step comprises:

a) grinding said sample in sodium hydroxide; and b) diluting said sample with Tris(hydroxymethyl) aminomethane buffer.

17. A method of screening plants for the presence of *Phytophthora cactorum*, comprising the steps of:

a) obtaining a plant sample;

b) lysing any fungal cells present in the strawberry sample to release fungal DNA;

c) amplifying any fungal DNA present by PCR using an oligonucleotide primer of SEQ ID NO:1 and an oligonucleotide primer of SEQ ID NO:3; and d) digesting any approximately 600 base pair amplification product from step (c) with HaeIII, endonuclease;

wherein digestion of an approximately 600 base pair amplification product by HaeIII endonuclease indicates the presence of *P. cactorum* in the plant sample.

18. The method of claim 17 wherein said plant sample is obtained from the group consisting of apple fruit, apple plants, strawberry fruit, and strawberry plant.

19. The method of claim 17 wherein said lysing step comprises:

a) grinding said sample in sodium hydroxide; and b) diluting said sample with Tris(hydroxymethyl) aminomethane buffer.

20. A kit for screening samples for the presence of at least one of the Phytophthora species selected from the group consisting of *Phytophthora infestans*, *Phytophthora cactorum*, and *Phytophthora mirabilis*, comprising an oligonucleotide of SEQ ID NO:1.

21. A kit according to claim 20, further comprising at least one of an oligonucleotide primer of SEQ ID NO:3 and HaeIII restriction endonuclease.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( x i ) SEQUENCE DESCRIPTION: SEQ ID NO:1:

CTCGCTACAA TAGGAGGGTC  20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( x i ) SEQUENCE DESCRIPTION: SEQ ID NO:2:

TCCTCCGCTT ATTGATATGC  20

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( x i ) SEQUENCE DESCRIPTION: SEQ ID NO:3:

GGAAGTAAAA GTCGTAACAA GG  22